(12) United States Patent
Du Boisson et al.

(10) Patent No.: US 7,259,281 B2
(45) Date of Patent: *Aug. 21, 2007

(54) FLUOROBUTENE DERIVATIVES AND PROCESS FOR PRODUCING SAME

(75) Inventors: Richard A. Du Boisson, Gainesville, FL (US); Adam C. Alty, Gainesville, FL (US)

(73) Assignee: Central Glass Company, Limited, Ube-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/506,963

(22) Filed: Aug. 21, 2006

(65) Prior Publication Data

US 2006/0281955 A1    Dec. 14, 2006

Related U.S. Application Data

(62) Division of application No. 10/424,982, filed on Apr. 29, 2003, now abandoned.

(51) Int. Cl.
C07C 17/00        (2006.01)
(52) U.S. Cl. .................................................... 570/126
(58) Field of Classification Search ................ 570/136
See application file for complete search history.

(56) References Cited

U.S. PATENT DOCUMENTS 2,480,560 A * 8/1949 Downing et al. ........... 570/149
2,599,631 A   6/1952 Harmon et al.
2,750,431 A   6/1956 Tarrant et al.

FOREIGN PATENT DOCUMENTS

WO   WO 2004/058827 A1   7/2004

OTHER PUBLICATIONS

Haszeldine et al., addition of free radicals to unsaturated systems, (Journal of Chemical Society (1954) 2040-2042.
Anderson et al., Diels-Alder reaction, (Journal of Chemical [section] C: (1969), (2), 211-217.
European Search Report dated Aug. 31, 2006 (three (3) pages).

* cited by examiner

*Primary Examiner*—Johann Richter
*Assistant Examiner*—Kellette Gale
(74) *Attorney, Agent, or Firm*—Crowell & Moring LLP

(57) ABSTRACT

The present invention provides novel compounds 2,4,4,4-tetrafluoro-1-butene and (E)- and (Z)-1,1,1,3-tetrafluoro-2-butenes. Furthermore, the present invention provides the following novel first and second processes for producing 2,4,4,4-tetrafluoro-1-butene and (E)- and (Z)-1,1,1,3-tetrafluoro-2-butenes. The first process is a process for producing 2,4,4,4-tetrafluoro-1-butene by heating 1,1,1,3,3-pentafluorobutane at from about 200° C. to about 700° C. The second process is a process for producing (E)- and (Z)-1,1,1,3-tetrafluoro-2-butenes by bringing 1,1,1,3,3-pentafluorobutane with a base. By the first and second processes, it is possible to obtain respective target fluorobutenes with high selectivity.

7 Claims, No Drawings

FLUOROBUTENE DERIVATIVES AND PROCESS FOR PRODUCING SAME

CROSS REFERENCE TO RELATED DOCUMENTS

The present application is a division of application Ser. No. 10/424,982, filed Apr. 29, 2003 now abandoned, whose disclosure is hereby incorporated by reference in its entirety into the present application.

This specification contains subject matter in common with Disclosure Document No. 492915 entitled "Thermal Dehydrofluorination of HFC's" submitted by Adam C. Alty and Richard A. Du Boisson to the United States Patent and Trademark Office on May 1, 2001, and hereby claims all benefits legally available from said disclosure document. In addition, the contents of said disclosure documents are incorporated herein by reference.

BACKGROUND OF THE INVENTION

The present invention relates to novel fluorobutenes. Furthermore, it relates to a process for producing a fluorobutene by a dehydrofluorination with a raw material of a polyfluorobutane.

Fluorobutenes are useful as monomers for fluorine-containing polymers, synthesized intermediate s/building blocks for producing fluorine-containing intermediates, and raw materials for producing hydrofluorocarbons.

Thermal dehydrofluorination is a well-known process for synthesizing olefins. Dehydrochlorination is widely used for forming a carbon-carbon multiple bond. Furthermore, there are several examples of thermal dehydrochlorination process used for producing fluoroolefins. On the other hand, almost all of thermal dehydrofluorinations are impractical based on a general knowledge due to their low conversion and low selectivity.

As its theoretical background, there is provided that the energy necessary for severing a C—F bond is close to that necessary for severing a carbon-carbon bond since the carbon-fluorine bond is very strong. In general, the temperature necessary for releasing hydrogen fluoride (HF) is far higher than the temperature for dehydrochlorination of an analogous substance containing chlorine atom instead at the defluorination site. Under a high temperature condition necessary for conducting the dehydrofluorination, molecular decomposition reactions and rearrangement reactions compete, thereby lowering selectivity. U.S. Pat. No. 2,480,560 describes that non-catalytic dehydrofluorinations of five different hydrofluorocarbons give fluoroolefins with low selectivity.

Even in the examination process in relation to the present invention of the present inventors, when 1,1,1,4,4,4-hexafluorobutane (HFC-356mf) had been added to a nickel reaction tube at 630° C., it mainly gave trifluoromethane and 3,3,3-trifluoropropene with a conversion of 56%, and it was not possible to obtain 1,1,4,4-pentafluoro-1-butene, which is considered to be formed by dehydrofluorination (Comparative Example 1). Furthermore, when 2-trifluoromethyl-1,1,1-trifluoropropane was similarly treated at 660° C., it mainly gave trifluoromethane and 3,3,3-trifluoropropene, and it was not possible to obtain 2-trifluoromethyl-1,1-difluoropropene, which is considered to be formed by dehydrofluorination (Comparative Example 2).

In order to overcome such problems and to efficiently produce fluoroolefins, much effort has been made in the development of catalytic dehydrofluorination. By catalytic process, it may be possible that hydrogen fluoride is released at a temperature lower than that at which the above side reactions become noticeable, thereby causing an expectation for improving selectivity. U.S. Pat. No. 2,599,631 describes both of thermal (non-catalytic) and catalytic processes for producing vinyl fluoride by dehydrofluorination of 1,1-difluoroethane and shows that the catalytic process is more useful. However, one of big problems of the catalytic dehydrofluorination process is a rapid deactivation of the catalyst due to by-products and polymerization products.

Another means for producing fluoroolefins by dehydrofluorination is a process by contact with a base. However, in general, a base-used dehydrofluorination gives in many cases isomers that are different from products obtained by a thermal dehydrofluorination process, and therefore it has been difficult to say that it is an efficient production process of necessary fluoroolefins.

SUMMARY OF THE INVENTION

It is an object of the present invention to provide 2,4,4,4-tetrafluoro-1-butene and (E)- and (Z)-1,1,1,3-tetrafluoro-2-butenes, which are novel fluoroolefins. It is another object of the present invention to provide an industrially achievable process for producing these compounds.

In order to solve the above problems, the inventors have eagerly conducted an examination on reaction systems applicable to thermal (non-catalytic) dehydrofluorinations. As a result, it was surprisingly found that 1,1,1,3,3-pentafluorobutane gives 2,4,4,4-tetrafluoro-1-butene, which is a novel fluorine-containing compound and becomes a raw material for useful fluorine-containing synthesis intermediates, highly selectively with high conversion by a thermal, non-catalytic dehydrofluorination. It was also found that conversion and selectivity of the reaction particularly improve under a specific condition such as passing through a heated reaction tube ("a first process").

The present inventors further found that (E)- and (Z)-1,1,1,3-tetrafluoro-2-butenes, which are novel compounds, are given by heating 1,1,1,3,3-pentafluorobutane and that selectivity of (E)- and (Z)-1,1,1,3-tetrafluoro-2-butenes particularly improves by bringing 1,1,1,3,3-pentafluorobutane with a base ("a second process"), thereby completing the present invention.

That is, the present invention provides 2,4,4,4-tetrafluoro-1-butene and (E)- and (Z)-1,1,1,3-tetrafluoro-2-butenes, which are useful novel compounds as fluorine-containing intermediates, using a low-price polyfluorobutane as the raw material and using a thermal (non-catalytic) dehydrofluorination and a base-contact dehydrofluorination. Furthermore, the present invention provides processes for producing these 2,4,4,4-tetrafluoro-1-butene and (E)- and (Z)-1,1,1,3-tetrafluoro-2-butenes, which can be conducted in an industrial scale.

The first process and the second process of the present invention are respectively summarized as the following formulas 1 and formula 2.

Formula 1:

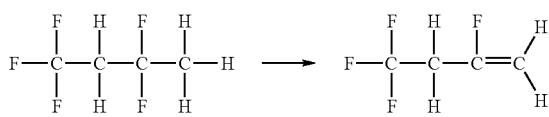

Formula 2:

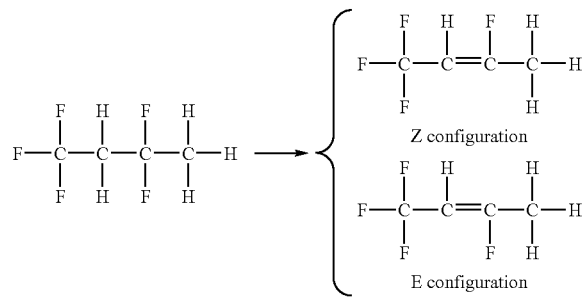

-continued

DESCRIPTION OF THE PREFERRED EMBODIMENTS

In the following, the present invention is explained in detail. Firstly, the first process of the present invention, a production of 2,4,4,4-tetrafluoro-1-butene by a thermal, non-catalytic dehydrofluorination of 1,1,1,3,3-pentafluorobutane, is described. This butene is a novel substance, its production has not been described up to now, and it is a synthesis raw material of fluorine-containing intermediates useful in the fields of medicines and agricultural chemicals.

This first process is achieved by heating 1,1,1,3,3-pentafluorobutane, which is industrially available as 365mfc, at from about 200° C. to about 700° C. As to the temperature of this dehydrofluorination, it can generally be conducted in a range of about 200° C. to about 700° C., preferably 300° C.-600° C. It is effective to maintain the reaction temperature in a range of 400° C.-550° C. in order to obtain the optimum conversion and selectivity.

It is preferable to conduct the first process under a substantially base-free condition (i.e., under an acid or neutral condition). Herein, "base" refers to a substance known as a basic substance. For example, a compound showing a pH of 8 or higher, when dissolved in water to a have a concentration of 0.1 mol dm$^{-3}$, corresponds thereto. Even when the reaction is conducted under a condition under which such base is not coexistent, the cleavage of a carbon-carbon bond is prevented, and it is possible to obtain 2,4,4,4-tetrafluoro-1-butene with high selectivity.

The reaction manner of the first process is either flow type or batch type. In many cases, it is possible in the reaction to obtain a preferable selectivity by subjecting 1,1,1,3,3-pentafluorobutane to a high-temperature treatment for a relatively short time. Therefore, flow type is more preferable. It becomes necessary in general to have pressurization in the reaction of batch type. In contrast, the reaction of flow type proceeds sufficiently under normal pressure. Therefore, flow type is advantageous from the viewpoint of operability.

In the case of batch type, there is considered a process in which 1,1,1,3,3-pentafluorobutane is introduced into a reactor that is resistant against the pressurization condition and against the contact with hydrogen fluoride, followed by sealing and heating with stirring. Upon this, it is desirable that the inside sample is occasionally sampled, that the analysis is conducted by a method such as gas chromatography, and that the reaction step is terminated at the time when the raw material has sufficiently been consumed and converted into the product.

In contrast with this, the flow-type reaction is achieved by heating and vaporizing 1,1,1,3,3-pentafluorobutane and by allowing it to flow through a thermal reaction tube. The thermal reaction tube must be constructed from a material that is resistant against the contact with hydrogen fluoride even at high reaction temperature. In some cases, this is filled with a filler that has resistance against hydrogen fluoride, in order to improve the mixing effect and the thermal contact, and that is preferable in general. For example, although it is possible to use a nickel alloy for the reaction tube and Monel Pro-pack for the filler, it is not limited to this.

In the following, in the present specification the term "raw material input standard contact time" is defined as follows. That is, "the value obtained by subtracting the solid phase volume occupied by the filler from the inside volume of the reaction tube" is referred to as "column volume", and in the following it is represented by A, too. On the other hand, "the volume of the raw material gas introduced into the reaction tube per second" is represented by B. The value of B is calculated from mol number of the raw material introduced per second, from pressure and from temperature, assuming that the raw material gas is ideal gas. Upon this, the value (=A/B) obtained by dividing A by B is referred to as "raw material input standard contact time". In the reaction tube, HF and other gases are produced as by-products, and the mole number change occurs. However, these are not taken into consideration upon calculating "contact time". The contact time of the reaction gas in ideal condition in which selectivity of the dehydrofluorination is 100% with 100% conversion becomes a half of the raw material input standard contact time herein referred to.

The thus calculated "raw material input standard contact time" is not particularly limited. In the case of maintaining the reaction temperature in a range of 400° C.-550° C. as mentioned above, from about 60 column volume to 300 column volume per hour (about 12 seconds to 60 seconds in raw material input contact time) is preferable. The introduction with from about 90 column volume to about 200 column volume per hour (about 18 seconds to 40 seconds in raw material input contact time) is more preferable. On the other hand, when the raw material input contact time exceeds 200 seconds, side reactions tend to occur. When the raw material input contact time is less than 1 second, conversion is low. Therefore, it is not preferable.

From the above, under a base-free condition, the passing of 1,1,1,3,3-pentafluorobutane through a reaction tube heated at 400° C.-550° C. with an input raw material contact time of from 18 second to 40 seconds is a particularly preferable embodiment in the first process of the present invention.

The optimum contact time depends on the temperature (reaction temperature), shape and filler of the reaction tube. Therefore, it is desirable to set the optimum value by suitably adjusting the raw material supply rate (raw material input contact time) for each set temperature, each reaction tube shape and each filler type. In conducting the present invention, a person skilled in the art is not prevented from such optimization. In general, the adoption of a contact time capable of obtaining a raw material conversion of 25% or higher is preferable from the viewpoint of the recovery and the reuse of the unreacted raw material. More preferably, it is adjusted so that the conversion becomes 70% or more.

Although the reaction pressure may be lower or higher than the atmospheric pressure or under atmosphere, under the atmospheric pressure is generally preferable. It is also possible to conduct the reaction in the presence of an inert gas (such as nitrogen and argon) that is stable under the reaction conditions or in the presence of an excessive HF.

The dehydrofluorination process of this invention can be conducted in a gas phase using a well-known chemical engineering apparatus. The reaction tube, a related raw-material introduction system, an outflow system and a related unit are made of a material strong against hydrogen fluoride. As typical materials, particularly stainless steel material such as austenite-type, or high nickel alloy and copper clad steel such as Monel nickel-copper alloy, Hastelloy nickel alloy and Inconel nickel-chromium alloy can be exemplified. However, it is not limited to this.

In a reaction mixture obtained by the first process, 1,1,1,3,3-pentafluorobutane (the raw material) and (E)- and (Z)-1,1,1,3-tetrafluoro-2-butenes (by-products) are coexistent with the target product, 2,4,4,4-tetrafluoro-1-butene. However, the present inventors found that these compounds have boiling points sufficiently different from each other and do not cause azeotropic phenomena (2,4,4,4-tetrafluoro-1-butene boiling point: 29-30° C., 1,1,1,3,3-pentafluorobutane boiling point: 40° C., (E)-1,1,1,3-tetrafluoro-2-butene: 18-19° C., and (Z)-1,1,1,3-tetrafluoro-2-butene: 48-49° C. Each is the boiling point at atmospheric pressure.)

Therefore, it is possible to isolate the target 2,4,4,4-tetrafluoro-1-butene with high purity by obtaining a reaction mixture by the first process and then by subjecting this reaction mixture to distillation. Although there are no particular limitations on the conditions of this distillation, it is the simplest to conduct that at normal pressure. According to the present invention, it is possible to easily isolate the target 2,4,4,4-tetrafluoro-1-butene without conducting a complicated purification operation after the reaction. Therefore, it is particularly advantageous in producing 2,4,4,4-tetrafluoro-1-butene industrially.

Furthermore, after recovery of the unreacted starting material (1,1,1,3,3-pentafluorobutane), its reuse becomes possible by introducing it again into the reactor.

Next, the second process of the present invention, a process for highly selectively providing (E)- and (Z)-1,1,1,3-tetrafluoro-2-butenes by dehydrofluorinating 1,1,1,3,3-pentafluorobutane, is described in detail.

As mentioned in the first process, it is possible to obtain (E)- and (Z)-1,1,1,3-tetrafluoro-2-butenes together with 2,4,4,4-tetrafluoro-1-butene (a main product) by subjecting 1,1,1,3,3-pentafluorobutane to a heating treatment at from about 200° C. to about 700° C.

However, the inventors found that it is particularly effective to bring 1,1,1,3,3-pentafluorobutane into contact with a base to dehydrofluorinate it, thereby obtaining (E)- and (Z)-1,1,1,3-tetrafluoro-2-butenes with higher selectivity and yield.

Hereinafter, a dehydrofluorination of 1,1,1,3,3-pentafluorobutane using a base is described in detail. (E)- and (Z)-1,1,1,3-tetrafluoro-2-butenes are novel compounds, and there have been no synthesis reports in the past. These are isomers of 1-butene obtained from the above-described thermal dehydrofluorination. The above-mentioned thermal dehydrofluorination of 1,1,1,3,3-pentafluorobutane (the first process) and a dehydrofluorination of 1,1,1,3,3-pentafluorobutane by a base (the second process) are complementary, and it becomes possible to produce useful, different positional isomers of tetrafluorobutene.

Although there are no particular limitations on the base to be used, it is possible to cite alkali metal hydroxides (potassium hydroxide, sodium hydroxide, lithium hydroxide and the like), alkali metal carbonates (sodium carbonate, potassium carbonate, sodium hydrogencarbonate, potassium hydrogencarbonate and the like), alkali earth metal hydroxides (calcium hydroxide, magnesium hydroxide and the like), organic bases (tertiary amines such as triethylamine, tributylamine, and trimethylamine; primary amines such as monoethylamine, monobutylamine, cyclohexylamine, and aniline; secondary amines such as diethylamine and dibutylamine; aromatic bases such as pyridine, picoline, lutidine, and ethylpyridine; and strong bases such as guanidine and 1,8-diazabicyclo[5.4.0]dec-7-ene (DBU)) or other strong bases (such as sodium methoxide, sodium ethoxide, potassium methoxide, and potassium ethoxide) that are commonly used in analogous reactions. Of these, potassium hydroxide, sodium hydroxide and calcium hydroxide and the like of low prices are particularly preferable.

Although the reaction is achieved by bringing the raw material 1,1,1,3,3-pentafluorobutane with a base, it is desirable to gradually mix both in order to maintain the reaction conditions mildly. For example, it is possible to cite a process such as a gradual addition of the raw material 1,1,1,3,3-pentafluorobutane with stirring of a base-containing liquid. On the contrary, it is also possible to allow the reaction to proceed by adding a base to the raw material 1,1,1,3,3-pentafluorobutane. The base can be used as an aqueous solution or a simple substance, and it is possible to add a phase transfer catalyst. For example, since 85% potassium hydroxide melts by heating to 100° C. or higher, it is convenient that this liquid in the melted condition is stirred and the raw material 1,1,1,3,3-pentafluorobutane is added dropwise thereto.

The base may be used as a solution by dissolving it in a solvent. As the solvent of this case, there may be used water, ethers (e.g., diethyl ether, dibutyl ether, methyl butyl ether, phenetole, dioxane, tetrahydrofuran, tetrahydropyran, anisole, benzyl ether, glymes (e.g., monoglyme, diglyme, and triglyme)) and halogen-containing solvents (e.g., methylene chloride, 1,1-dichloroethane, 1,2-dichloroethane, chloroform, carbon tetrachloride, chlorobenzene, 1,4-bis(trifluoromethyl)benzene) and the like. In other cases, it may be preferable to use in the reaction a commonly-used phase-transfer catalyst (e.g., 18-crown-6, dibenzo-18-crown-6, dicyclohexano-18-crown-6, 12-crown-4, 15-crown-5, dibenzo-24-crown-8, tetraethylammonium chloride, tetraethylammonium bromide, tetrabutylammonium chloride, tetrabutylammonium bromide, ethyltributylammonium bromide, tetraphenylammonium bromide, and tetraphenylphosphonium bromide).

Although there are no particular limitations on the reaction temperature of the process for producing (E)- and (Z)-1,1,1,3-tetrafluoro-2-butenes by the contact with this base, from 0° C. to 300° C. is preferable, and more preferably it is a range of from 30° C. to 250° C.

The reaction pressure may be lower or higher than atmospheric pressure. In general, the vicinity of atmospheric pressure is simple and preferable.

Although there are no particular limitations on the reaction time, the reaction is fast under a heated condition, and the reaction occurs immediately when the raw material and a base are mixed together. Therefore, as shown in the after-mentioned Example 2, a process is simple, in which mixing of the raw material and a base is conducted under an open condition (atmospheric pressure), and a mixed gas of the raw material and the product is cooled down, thereby collecting it as a liquid (reaction mixture).

However, it is not limited to such process. A dehydrofluorination process of the second process can be conducted by a batch manner or in a continuous reaction apparatus using a known chemical engineering technique. The apparatus and its related raw material introducing line, the outflow line, and related units should be made from a material that is resistant against strong bases. Typical examples of the material are stainless steel, carbon steel, or high nickel alloys such as Monel-nickel copper alloy, Hastelloy-nickel alloy and Inconel nickel-chromium alloy, and copper clad steel. In limited cases, it is possible to use glass or glass-lined steel.

Similar to the first process, it is also possible to separate each component from the reaction mixture obtained by this second process by a distillation operation. Specifically, it is possible to isolate the unreacted 1,1,1,3,3-pentafluorobutane (boiling point=40° C.), (E)-1,1,1,3-tetrafluoro-2-butene (boiling point=18-19° C.), and (Z)-1,1,1,3-tetrafluoro-2-butene (boiling point=48-49° C.) as each distillate. Although there are no particular limitations on this distillation condition, it is the simplest to conduct it at normal pressure. Since by-products generated by the present reaction are low-boiling-point compounds such as butadiene and butyne, it is easy to separate these. Since it is possible to easily obtain (E)- and (Z)- 1,1,1,3-tetrafluoro-2-butenes of high purity, it is possible to obtain a high purity diastereomer by apply a diastereoselective reaction. Therefore, it is highly useful as a synthesis raw material.

The recovered raw material 1,1,1,3,3-pentafluorobutane can be reused as a reaction raw material of the first process or second process.

In the following, the present invention is illustrated in detail by examples. The present invention is not limited to these examples.

EXAMPLE 1

A nickel reaction tube of ¾ inches (1.905 cm) diameter and 36 inches (91.4 cm) total length (filled with 200 ml of nickel Propack (void ratio=96%) of 0.24 inches (0.61 cm)) was heated at temperatures shown in 1-1 to 1-4 of the following Table. Under these conditions, 1,1, 1,3,3-pentafluorobutane was vaporized by a vaporizer and was allowed to flow at a rate of 70 g/hr. The outflow gas, which had passed through the reaction tube, was passed through water in order to remove hydrogen fluoride (HF). Then, it was dried with calcium sulfate and collected, followed by analysis by gas chromatography (FID, hereinafter the same).

The inside volume of the reaction tube in the present example is 261 cm$^3$, and the volume ("column volume") except the solid phase section of the filler is 253 cm$^3$. The raw material input standard contact time is from 29 seconds (1-4) to 32 seconds (1-1).

The results were shown in Table. "GC %" refers to areal % of each component of the above reaction mixture measured by FID.

(1) $CF_3CH_2CF=CH_2$
a colorless, transparent liquid
$^1$H-NMR solvent: $CDCl_3$, standard substance: TMS
δ: 4.88 (dd, J=16.2 Hz, 3.5 Hz, 1H), 4.59 (dd, J=47.3 Hz, 3.5 Hz, 1H), 3.01(dq, J=16.7 Hz, 9.9 Hz, 2H)
$^{19}$F-NMR solvent: $CDCl_3$, standard substance: $CFCl_3$
δ: −66.2 (s, 3F), −95.5 ∼−96.5 (m, 1F)
$^{13}$C-NMR solvent:$CDCl_3$, standard substance: TMS
δ: 156.54 (d, J=254 Hz), 124.54 (q, J=277 Hz), 96.40(d, J=18.0 Hz),
37.63(dq, J=32 Hz, 30 Hz)
GLC-MS
m/z (rel. intensity), 128(M$^+$, 75.2), 113(5.6), 109(9.2), 95(7.6), 89(23.2), 77(9.6), 75(3.2), 69(22.8), 64(100), 59(68.8), 51(13.6), 45(16.4)

(2) (E)-$CF_3CH=CFCH_3$
a colorless, transparent liquid
$^1$H-NMR solvent: $CDCl_3$, standard substance: TMS
δ: 5.44 (dq, J=16.9 Hz, 7.6 Hz, 1H), 2.14 (d, J=18.7 Hz, 3H)
$^{19}$F-NMR solvent:$CDCl_3$, standard substance: $CFCl_3$
δ: −57.2 (s, 3F), −79.5 (s, 1F)
GLC-MS
m/z (rel. intensity), 128(M$^+$, 44.0), 113(70.4), 109(32.0), 89(29.2), 78(12.8), 77(23.6),69(22.4), 64(22.8), 59(29.6), 57(24.4), 51(18.8), 45(14.8), 39(100)

(3) (Z)-$CF_3CH=CFCH_3$
a colorless, transparent liquid
$^1$H-NMR solvent: $CDCl_3$, standard substance: TMS
δ: 5.00 (dq, J=32.7 Hz, 7.6 Hz, 1H), 1.99 (d, J=18.7 Hz, 3H)
$^{19}$F-NMR solvent:$CDCl_3$, standard substance: $CFCl_3$
δ: −58.9 (dd, J=17.1 Hz, 6.4 Hz, 3F), −83.2∼−83.7 (m, 1F)
GLC-MS
m/z (rel. intensity), 128(M$^+$, 44.0), 113(72.0), 109(37.2), 89(31.2), 78(11.6), 77(25.6), 69(25.6), 64(22.4), 59(29.6), 57(25.2), 51(20.0), 45(15.2), 39(100)

EXAMPLE 2

A (polytetrafluoroethylene) coating magnetic stirring bar, a dropping funnel (under the liquid level), and a Vigreux column were attached to a 250 ml flask. The outlet of the column was passed into an oil bubbler, and it was connected to a collector cooled down to −78° C. 80 g of 85% potassium hydroxide (in the form of flakes) were added to the flask, and it was heated to 210° C. using an oil bath, followed by gradual dropping of 1,1,1,3,3-pentafluorobutane. The products and the unreacted raw material were collected by the collector. The obtained mixture contained seven kinds of

TABLE

| No. | Temp. ° C. | 365mfc GC % | $CF_3CH_2CF=CH_2$ GC % | (E)-$CF_3CH=CFCH_3$ GC % | (Z)-$CF_3CH=CFCH_3$ GC % |
|---|---|---|---|---|---|
| 1-1 | 450 | 73.7 | 18.6 | 3.8 | 2.7 |
| 1-2 | 470 | 69.5 | 23.4 | 4.3 | 2.8 |
| 1-3 | 500 | 63.5 | 29.6 | 4.3 | 1.3 |
| 1-4 | 520 | 36.4 | 56.9 | 3.4 | 1.6 |

The products were identified by mass spectrometry and NMR (1H, 19F and 13C) and isolated with a purity of 97% by distillation (boiling point: 29-30° C.) under normal pressure. The data are written in the following.

products in addition to the raw material. In gas chromatograph area at the reaction termination, the raw material was in 50%, (E-) configuration was in 17.8%, (Z-) configuration was in 17.8%, $CF_3CH_2CF=CH_2$ was in 8.0%, and the remainder of 6.4% was a mixture containing butadiene and butyne. It was possible to easily separate (E)-CF$_3$CH=CFCH$_3$ (boiling point: 18-19° C.) and (Z)-CF$_3$CH=CFCH$_3$ (boiling point: 48-49° C.) with a purity of 98% or higher by distillation. These structures were identified by mass spectroscopy and NMR.

Comparative Example 1

A nickel reaction tube of ¾ inches (1.91 cm) diameter and 36 inches (91.4 cm) total length was heated to 630° C., and the reaction tube was filled with a nickel Pro-pack (void ratio=96%) of 0.24 inches (0.61 cm)) for the purpose of obtaining higher mixing effect and heat transfer effect. In this condition, 1,1,1,4,4,4-hexafluorobutane was gasified by the same process as that of Example 1 and introduced at a flow rate such that the contact time became 30 seconds. The gas, which had passed the tube, was passed through water in order to remove hydrogen fluoride (HF), followed by drying with calcium sulfate and then gas chromatograph analysis.

As a result, the gas chromatograph area of the raw material 1,1,1,4,4,4-hexafluorobutane was 43.2%, and 30.6% 3,3,3-trifluoropropene and 17.1% trifluoromethane were additionally detected. The target 1,1,4,4,4-pentafluoro-1-butene was not detected.

Comparative Example 2

Using the same apparatus as that of Comparative Example 1, 2-(trifluoromethyl)-1,1,1-trifluoropropane was introduced in the form of gas at 660° C. As a result of conducting the GC analysis of the outflow gas, the raw material was in 18.9%, 3,3,3-trifluoropropene was in 24.5%, and trifluoromethane was in 43.5%. The target 2-trifluoromethyl-1,1-difluoropropene was not detected.

What is claimed is:

1. A process for producing 2,4,4,4-tetrafluoro-1-butene, comprising heating 1,1,1,3,3-pentafluorobutane at from about 200° C. to about 700° C.

2. A process for producing 2,4,4,4-tetrafluoro-1-butene according to claim 1, comprising that the heating of claim 1 is conducted under a condition that is substantially free of a base.

3. A process for producing 2,4,4,4-tetrafluoro-1-butene according to claim 1, comprising that the heating is conducted by passing 1,1,1,3,3-pentafluorobutane through a reaction tube heated at from about 200° C. to about 700° C.

4. A process for producing 2,4,4,4-tetrafluoro-1-butene according to claim 3, comprising that the heating is conducted by passing 1,1,1,3,3-pentafluorobutane through a reaction tube heated at from about 200° C. to about 700° C.

5. A process for producing 2,4,4,4-tetrafluoro-1-butene, comprising that 1,1,1,3,3-pentafluorobutane is passed through a reaction tube heated at 400° C.-500° C. under a condition that is substantially free of a base.

6. A process for producing 2,4,4,4-tetrafluoro-1-butene according to claim 5, comprising that the passing of the 1,1,1,3,3-pentafluorobutane to the reaction tube according to claim 5 is conducted with an input raw material standard contact time of 18-40 seconds.

7. A process for producing and isolating 2,4,4,4-tetrafluoro-1-butene, comprising that a mixture containing 2,4,4,4-tetrafluoro-1-butene is obtained by a process of claim 1, and then the mixture is subjected to a distillation.

* * * * *